United States Patent [19]

Reiter

[11] Patent Number: 4,563,185
[45] Date of Patent: Jan. 7, 1986

[54] DISPOSABLE DIAPER HAVING ELASTICIZED WAISTBAND WITH NON-LINEAR SEVERED EDGE

[75] Inventor: Godfrey Reiter, Cincinnati, Ohio

[73] Assignee: The Procter & Gamble Company, Cincinnati, Ohio

[21] Appl. No.: 734,987

[22] Filed: May 17, 1985

Related U.S. Application Data

[62] Division of Ser. No. 549,345, Nov. 4, 1983, Pat. No. 4,543,154.

[51] Int. Cl.⁴ .............................................. A41B 13/02
[52] U.S. Cl. ................................................. 604/385 A
[58] Field of Search .................... 604/385, 385 A, 358, 604/369, 366, 370; 156/73.001

[56] References Cited

U.S. PATENT DOCUMENTS

| | | | |
|---|---|---|---|
| Re. 26,151 | 1/1967 | Duncan et al. | 128/284 |
| 2,737,701 | 3/1956 | Hubbard et al. | 28/74 |
| 2,904,841 | 9/1959 | Haugh | 18/48 |
| 3,245,407 | 4/1966 | Mason | 128/284 |
| 3,249,671 | 5/1966 | Perrone et al. | 264/209 |
| 3,256,558 | 6/1966 | Andersen et al. | 18/1 |
| 3,339,548 | 9/1967 | Seltzer | 604/385 |
| 3,395,706 | 8/1968 | Higgins et al. | 604/385 |
| 3,551,540 | 12/1970 | Pellicciari et al. | 264/89 |
| 3,560,292 | 2/1971 | Butter | 156/229 |
| 3,570,085 | 3/1971 | Heinemann | 28/72.2 |
| 3,575,782 | 4/1971 | Hansen | 161/141 |
| 3,584,103 | 6/1971 | Harris | 264/168 |
| 3,622,434 | 11/1971 | Newman | 161/128 |
| 3,639,917 | 2/1972 | Althouse | 2/228 |
| 3,663,962 | 5/1972 | Burger | 2/224 A |
| 3,694,815 | 10/1972 | Burger | 2/224 A |
| 3,755,062 | 8/1973 | Schirmer | 161/146 |
| 3,773,608 | 11/1973 | Yoshimura et al. | 161/168 |
| 3,805,299 | 4/1974 | Saad-Chujfi | 2/237 |
| 3,819,401 | 6/1974 | Massengale et al. | 156/85 |
| 3,860,003 | 1/1975 | Buell | 128/287 |
| 3,891,737 | 6/1975 | Marsh et al. | 264/95 |
| 3,912,565 | 10/1975 | Koch et al. | 156/85 |
| 3,951,150 | 4/1976 | Schaar | 128/287 |
| 3,990,450 | 11/1976 | Schaar | 128/287 |
| 3,995,637 | 12/1976 | Schaar | 128/287 |
| 3,995,638 | 12/1976 | Schaar | 128/287 |
| 3,995,640 | 12/1976 | Schaar | 128/287 |
| 4,014,338 | 3/1977 | Schaar | 128/287 |
| 4,035,534 | 7/1977 | Nyberg | 428/36 |
| 4,041,949 | 8/1977 | Kozak | 128/287 |
| 4,059,667 | 11/1977 | Pangonis | 264/289 |
| 4,081,301 | 3/1978 | Buell | 156/164 |
| 4,149,918 | 4/1979 | Cislak | 156/380.9 |
| 4,193,899 | 3/1980 | Brenner | 260/23.5 A |
| 4,207,364 | 6/1980 | Nyberg | 428/36 |
| 4,253,461 | 3/1981 | Strickland et al. | 128/287 |

List continued on next page

FOREIGN PATENT DOCUMENTS

| | | |
|---|---|---|
| 57-53345 | 3/1982 | Japan . |
| 866820 | 5/1961 | United Kingdom . |
| 2016262 | 10/1979 | United Kingdom . |

OTHER PUBLICATIONS

European Patent Application No. 82 200801.7–Aziz & Blaney, 6/29/82.

D. A. Williamson, *Polymers & Plastics*, Jun. 1970, pp. 169–174.

Sudo & Ichibara, *TAPPI Pap. Syn. Conf. Proc.*, Washington, D.C., 10/24–10/26, 1979.

*Primary Examiner*—John D. Yasko
*Attorney, Agent, or Firm*—E. Kelly Linman; John V. Gorman; Richard C. Witte

[57] ABSTRACT

A method of producing a disposable diaper or other article including an elastically contractible element such as a waistband which undergoes a joint severance operation with one or more of the layers comprising the article, yet which, upon the application of an external stimulus such as heat, will return to its molecularly unoriented, heat stable state and thereby impart both shirring and elasticization to the severed edge of the article in a direction substantially parallel to the overall orientation of the line of severance. Particularly preferred articles made utilizing said method are also disclosed.

1 Claim, 8 Drawing Figures

U.S. PATENT DOCUMENTS

| | | | |
|---|---|---|---|
| 4,261,782 | 4/1981 | Teed | 156/361 |
| 4,277,594 | 7/1981 | Matthews | 526/352 |
| 4,285,747 | 8/1981 | Rega | 156/164 |
| 4,300,967 | 11/1981 | Sigl | 156/164 |
| 4,303,571 | 12/1981 | Jansen et al. | 260/33.6 AC |
| 4,311,660 | 1/1982 | Barham et al. | 264/342 RE |
| 4,324,245 | 4/1982 | Mesek et al. | 128/287 |
| 4,337,771 | 7/1982 | Pieniak et al. | 128/287 |
| 4,352,355 | 10/1982 | Mesek et al. | 604/385 A |
| 4,405,397 | 9/1983 | Teed | 604/385 A |
| 4,437,860 | 3/1984 | Sigl et al. | 604/385 A |
| 4,447,240 | 5/1984 | Ito et al. | 604/385 A |
| 4,486,192 | 12/1984 | Sigl | 604/385 |
| 4,507,163 | 3/1985 | Menard | 156/164 |

DISPOSABLE DIAPER HAVING ELASTICIZED WAISTBAND WITH NON-LINEAR SEVERED EDGE

This is a division of application Ser. No. 549,345, filed on Nov. 4, 1983 now U.S. Pat. No. 4,543,154.

BACKGROUND OF THE INVENTION

1. Field of the Invention

The present invention concerns an improved method for producing elasticized articles at high speed.

The present invention has further relation to such a method wherein an elastically contractible element is applied while in a substantially untensioned, molecularly oriented, heat unstable condition, and is thereafter subjected to an external stimulus, such as heat, to impart shirring to the article.

The present invention has particular relation to an improved method for forming elasticized articles wherein the article is comprised of two or more layers of material, including at least one elastically contractible polymeric element secured thereto in a substantially untensioned, molecularly oriented, heat unstable condition, said article thereafter being cut along a non-linear line of serverance at a point coinciding with said elastically contractible element so as to divide said elastically contractible element into at least two portions which will, upon subsequent heat treatment, cause shirring and elasticization of each of the non-linear severed edges thus produced.

Finally, the present invention has relation to an article exhibiting a non-linear, shirred, elasticized edge formed by said method.

2. Background Art

Infants (and other incontinents) wear disposable diapers to receive and contain urine, feces, and other body fluids. Disposable diapers function both to contain the discharged materials and to isolate these materials from the body of the wearer and from the wearer's surroundings. Modern embodiments of disposable diapers frequently perform these tasks in a manner superior to that of traditional cloth diapers.

Disposable diapers normally comprise three elements: a liquid permeable topsheet designed to be placed next to the wearer's skin; a liquid impermeable backsheet which forms, in use, the outer surface of the diaper; and an absorbent element interposed between the topsheet and the backsheet.

The topsheet is frequently a hydrophobic non-woven fabric which is readily permeable to fluid. Its hydrophobicity tends to cause the surface in contact with the wearer's skin to be dry and the skin to be protected from fluids absorbed within the absorbent element.

The absorbent element receives and retains fluids which pass through the topsheet. It normally comprises a batt of airlaid wood pulp fibers.

The backsheet functions to contain fluids within the absorbent element, thereby protecting the wearer's outer garments and other surfaces from soiling by these fluids. Backsheets are commonly formed of fluid impermeable materials such as polyethylene film.

Disposable diapers having many different basic designs are known in the art. The prior art patents hereinafter cited in the Background Art portion of the present specification, all of which are hereby incorporated herein by reference, are exemplary of such structures.

Duncan and Baker in U.S. Pat. No. Re. 26,151, issued Jan. 31. 1967, descirbe and claim a disposable diaper which has achieved wide acceptance and commercial success. Buell, in U.S. Pat. No. 3,860,003, issued Jan. 14, 1975 and hereby incorporated herein by reference, describes and claims another disposable diaper which, too, has achieved wide acceptance and commercial success. The diaper taught by Buell differs from that taught by Duncan and Baker in many respects, not the least of which is the provision in the Buell diaper of elasticized (or contractible) leg cuffs. Strickland and Visscher in U.S. Pat. No. 4,253,461, issued on Mar. 3, 1981, describe and claim another form of disposable diaper, sometimes referred to as an incontinent brief, intended to be worn by adults.

Mesek et al. in U.S. Pat. No. 4,324,245, issued Apr. 13, 1982; Pieniak et al. in U.S. Pat. No. 4,337,771, issued July 6, 1982; Mesek et al. in U.S. Pat. No. 4,352,355, issued Oct. 5, 1982 and Sciaraffa et al. in U.S. Pat. No. 4,381,781, issued May 3, 1983, describe disposable diapers having elasticized cuffs and elasticized (or contractible) waistbands.

Imparting elasticization to discrete articles has taken various forms. One particularly preferred method for continuously attaching discrete stretched elastic strands to predetermined isolated portions of disposable absorbent products is disclosed in U.S. Pat. No. 4,081,301 issued to Buell on Mar. 28, 1978 and hereby incorporated herein by reference. The inventive concept disclosed in the Buell patent, in a broad sense, relates to the continuous adherence of discrete lengths of stretched elastic to predetermined portions of a continuously moving web at relatively high operating speeds and thereafter severing the elastic in the unadhered areas to produce elasticized structures having discrete strands of elastic adhered thereto at predetermined locations along their length. In a particularly preferred embodiment, the aforementioned process is utilized to apply discrete elastic legbands to a disposable diaper structure to provide improved containment and fit therein.

An alternative apparatus and method for attaching elastic strips during the manufacture of elastic leg disposable diapers is disclosed in U.S. Pat. No. 4,261,782 issued to Teed on Apr. 14, 1981. According to the process disclosed in the Teed patent, the elastic strips are fed in the direction of web travel and are alternately stretched and relaxed during the attachment process.

Still other approaches to providing shirred, elastic, flexible articles involve the application of an oriented elastic material to the article to be elasticized in an untensionsed state and thereafter subjecting the oriented elastic material to heat to cause shrinkage and consequently shirring by restoring the material to its unoriented and elastic state. Exemplary of such processes are those shown in U.S. Pat. No. 3,912,565 issued to Koch et al. on Oct. 14, 1975, U.S. Pat. No. 3,639,917 issued to Althouse on Feb. 8, 1972 and U.S. Pat. No. 3,819,401 issued to Massengale et al. on June 25, 1974.

Koch discloses a method wherein a thin layer of flexible polyurethane material, which is heat shrinkable in the desired direction of article shirring, is disposed in direct contact with at least one side of a flexible sheet material and attached thereto without any significant shrinkage or other distortion of such layer. Subsequently, the layer of polyurethane material is heated to cause shrinkage thereof, whereby the sheet material attached thereto is shirred. The thermoplastic polyurethane resins employed by Koch may be shaped into the desired layer by conventional procedures, as for example by extruding in a molten condition as a continuous stream, followed by rapid quenching of such stream as on a chill roll or in a bath of cool water or other liquid. The layer of polyurethane material thus formed may be collected for subsequent processing at a later stage or, in continuous operations, may be uniaxially stretched directly after its formation. This may be accomplished as by stretching such layer of polyurethane material longitudinally between spaced pairs of differential speed rolls; that is, with one such pair of rolls being rotated at a more rapid speed than the other of such pair of rolls. The uniaxially oriented layer of polyurethane material is preferably heat set by being brought to a temperature slightly above its second order phase transition temperature, permitted a limited relaxation, and then cooled to the temperature of the ambient atmosphere. Once cooled the layer is dimensionally stable. In the example disclosed in the Koch patent, lengths of the heat shrinkable, heat set tape created by the foregoing method are removed from a supply roll and are placed in direct contact with a garment body adjacent to the openings to be elasticized. The attached tape lengths are then heated to shrink the same and cause the portions of the article body to which they are attached to shirr or gather.

Similar approaches utilizing other elastomeric materials are disclosed in the aforementioned patents to Althouse and Massengale et al.

In order to facilitate economical production, and hence disposability, of articles such as disposable diapers, incontinent briefs and the like, it is essential that the means of elasticizing these articles be capable of high speed and great reliability. Since articles such as disposable diapers are typically produced by forming a continuous web of the articles interconnected to one another at their adjacent waistband portions, processes such as those disclosed in the aforementioned U.S. Pat. No. 4,081,301 to Buell have functioned well in the application of stretched elastic bands in a direction generally parallel to the direction of web travel to form elasticized leg cuffs.

However, when it is desired to apply an elastic element intended to cause shirring of the finished article in a direction generally perpendicular to the direction of web travel at high speed while the web is moving, the method generally disclosed in the commonly assigned, copending patent application of L. Richard Chapman and Wayne I. Fanta, Ser. No. 476,733, filed Mar. 18, 1983 and entitled "CONTINUOUS METHOD FOR ELASTICIZING DISCRETE ARTICLES CUT FROM A MOVING WEB IN A DIRECTION PERPENDICULAR TO WEB TRAVEL" is particularly preferred. Specifically, the aforementioned application of Chapman et al. discloses a method for continuously elasticizing articles such as disposable diapers, incontinent briefs, and the like by securing an elastically contractible element to a moving, interconnected web of said articles, said elastically contractible element causing discrete articles cut from the web to shirr in a direction substantially perpendicular to the direction of web travel. Said elastically contractible element is preferably applied to said moving web while in a substantially untensioned, molecularly oriented, heat unstable condition, and is thereafter subjected to an external stimulus, such as heat which causes shrinkage of the elastically contractible element in a direction substantially perpendicular to the direction of web travel and shirring of the diaper waistband. The application of heat is preferably done after the discrete articles have been cut from the web and are in a substantially untensioned state to impart shirring.

Quite unexpectedly, it has been found that when the method generally disclosed in the aforementioned patent application of Chapman et al. is operated at high speed using a crush type cutter, e.g., a rotating cylinder having one or more radially extending blades mounted at its periphery operating against a hard surfaced anvil roll, plastic flow of certain of the polymeric materials comprising the article, including the elastically contractible element which serves as the waistband, results during the cutting operation which separates the individual articles from the continuous web. The resultant plastic flow causes fusing of the elements comprising the diaper at the severed edges of the structure. The effect becomes most pronounced in situations where the web is folded into a predetermined cross-section, such as a c-fold or an e-fold, prior to severance, since more layers of material are fused to one another, thereby creating a stiffened edge at the point of severance. It has further been found that when the fused, severed edges are formed by means of a linear cut oriented substantially perpendicular to the direction of web travel, the application of an external stimulus, such as heat, to impart shrinkage of the heat unstable, elastically contractible element is rendered to a degree ineffective. This is believed due to the resistance imparted by the stiffened, fused, edges formed during the cutting operation.

Similar results are observed when cutting operations employing heat energy, e.g., a laser beam, are employed to sever discrete articles from the web of interconnected articles.

Accordingly, it is an object of the present invention to produce a disposable diaper or other article incorporating an elastically contractible element such as a waistband which undergoes a joint severance operation with one or more of the layers comprising the article, yet which, upon the application of an external stimulus such as heat, will return to its molecularly unoriented, heat stable state and thereby impart both shirring and elasticization to the severed edge of the article in a direction substantially parallel to the overall orientation of the line of severance.

It is a further object of the present invention to provide a method of severing discrete diapers or other articles from a continuous web of said diapers or articles such that the stiff columnar effect created at the severed edge by fusing of the layers comprising the diaper or article to one another is minimized.

DISCLOSURE OF THE INVENTION

The present invention, in a particularly preferred embodiment, pertains to a continuous, high speed method for elasticizing articles such as disposable diapers, incontinent briefs and the like by securing an elastically contractible polymeric element to a moving interconnected web of said articles, said elastically contractible polymeric element causing discrete articles cut from the web to shirr in a direction substantially parallel to the overall orientation of the line of severance. In the particularly preferred embodiment herein disclosed, the line of severance and hence the desired direction of article shirring is oriented substantially perpendicular to the direction of web travel. The elastically contractible element is preferably applied to the moving web while in a substantially untensioned, molecularly oriented, heat unstable condition. The web is thereafter severed into discrete articles at points coinciding with the elastically contractible elements so as to divide each elastically contractible element into two discrete portions, one portion remaining with a severed edge of each of the articles to be elasticized.

In a particularly preferred embodiment, the method of the present invention is used to produce a disposable diaper which is, at least in part, held in its shaped configuration by the shaped elastically contractible waistband. The elastically contractible waistband is itself specifically formed and comprises an elastomeric material which has both a dimensionally heat unstable state and a dimensionally heat stable and elastic state (hereinafter referred to for convenience, simply as "elastomeric material"). "Elastic", as used herein describes a material which can be elongated to a practical extent upon the application of tension and which will substantially return to its original configuration after the tension is released. In the context of the present invention, the heat stable state is dimensionally smaller than the heat unstable state.

In a particularly preferred embodiment of the present invention the dimensionally heat unstable elastic material can be prepared by techniques such as tentering in a direction perpendicular to the direction of web travel. The web of heat unstable elastomeric material is thereafter continuously fed in the same direction as the web of interconnected diapers, and discrete segments of the heat unstable elastomeric web are severed and applied to each disposable diaper while the elastomeric material is in its heat unstable state. Because the length of each elastomeric waistband element in the diaper corresponds to the width of the elastomeric web from which the elements are cut, the direction of shrinkage of the elastomeric elements upon heating is substantially perpendicular to the direction of web travel.

Diapers to be elasticized in accordance with the present invention are cut from the web at points coinciding with said elastomeric elements along a line of severance which is nonlinear. Thus, a portion of each elastically contractible element remains secured to each of the severed edges The elastically contractible elements are thereafter subjected to an external stimulus, such as heat, in a substantially untensioned state to cause the elastomeric elements to shrink in a direction substantially parallel to their length, i.e., substantially parallel to the orientation of said line of severance, and assume a heat stable and elastic state. The nonlinear line of severance minimizes the columnar resistance imparted by the fused, severed edge of the diaper, thereby permitting shrinkage of the heat shrinkable elastomeric element and consequently a return to its heat stable and elastic state. In the illustrated embodiment, the resulting shirred, elastically contractible waistband assumes an essentially permanent set related to the folded configuration, such that even when the fused overlapping edges of the structure are separated, the essentially permanent set tends to cause the disposable diaper to be shaped and to fit more closely about the trunk of the wearer. The nonlinear severed edge of the resulting waistband is not only aesthetically pleasing, but feels soft against the wearer's skin.

BRIEF DESCRIPTION OF THE DRAWINGS

While the specification concludes with claims particularly and distinctly claiming the present invention, it is believed the present invention will be better understood from the following description in conjunction with the accompanying drawings in which:

DETAILED DESCRIPTION OF THE INVENTION

For purposes of illustration, the method of the present invention will be described in relation to the continuous fabrication of disposable diaper structures having elasticized waistbands, wherein its benefits are readily apparent. It is of course recognized that the invention may be practiced to advantage to produce elasticized articles in many alternative forms which are defined by the claims appended hereto.

Disposable diapers typcially comprise three major elements: a topsheet; a backsheet; and an absorbent element. The topsheet forms the inside of the disposable diaper (i.e., that portion intended to be placed next to the wearer's skin). The backsheet generally forms the exterior surface of the disposable diaper. The absorbent element is interposed between the topsheet and the backsheet.

A disposable diaper is generally designed to be placed between and generally centered between the legs of an infant and secured about the infant by bringing the front portion of the diaper adjacent the front waist area of the infant and the rear portion of the diaper adjacent the rear waist of the infant and securing the diaper in that position.

Optionally, disposable diapers comprise fastening tapes for securing the diaper about the infant. They also optionally comprise elastic members in the longitudinally extending margins to form an elastically contractible leg cuff or side flap. For example, see U.S. Pat. No. 3,860,003 issued to Buell on Jan. 14, 1975 and incorporated herein by reference. They also optionally comprise elastic elements in the laterally extending margins to form elastically contractible waistbands.

The waistband of a disposable diaper is that portion of the diaper which is intended to be placed adjacent the wearer's waist. While the waistband can comprise a separate element affixed to the body of the disposable diaper, it more often is an extension of other elements of the disposable diaper such as the backsheet or the topsheet or both the backsheet and the topsheet. Further, the waistband is generally considered to be that portion of the diaper extending from the laterally extending margin of the diaper to about the laterally extending margin of the absorbent element. Disposable diapers are normally constructed so as to have two waistbands: a front and a rear.

In the diaper embodiment herein disclosed for purposes of illustration, the elastically contractible waistband comprises an elastomeric material having both a heat unstable state and a heat stable and elastic state. The elastomeric material is attached to the disposable diaper when in its heat unstable state and is thereafter subjected to heating under conditions hereinafter defined in such a manner that it assumes its heat stable and elastic state.

Elastomeric materials of a type useful in the present invention include a number of materials well known to those skilled in the art. For example, the polyurethane described in the hereinbefore incorporated patent to Koch et al. and the plasticized vinyl chloride described in the hereinbefore incorporated patent to Massengale et al. can be used. Further, the compositions comprising a mixture of a thermoplastic resin material (or other organic, normally solid heat flowable material) in an elastomeric material as described by Cook in U.S. Pat. No. Re. 28,688, incorporated herein by reference, can also be used.

One particularly preferred elastomeric material useful herein is a film comprising a blend of ethylene propylene rubber with ethylene vinyl acetate, such as that available from Exxon Chemical Company of Florham Park, N.J. Specific film-forming thermoplastic elastomeric polymer compositions which are described as being suitable for forming webs capable of exhibiting heat stable and heat unstable states are disclosed in U.S. Pat. No. 4,303,571 issued to Jansen et al. on Dec. 1, 1981 and hereby incorporated herein by reference. The film is preferably converted to a dimensionally heat unstable state via molecular orientation by laterally stretching it while at an elevated temperature which is less than its crystalline melting temperature and allowing it to cool. This is generally done by means of a tentering apparatus, i.e., an apparatus designed to stretch the film in a direction perpendicular to the direction of web travel, as generally shown in FIG. 1.

Figure 1:
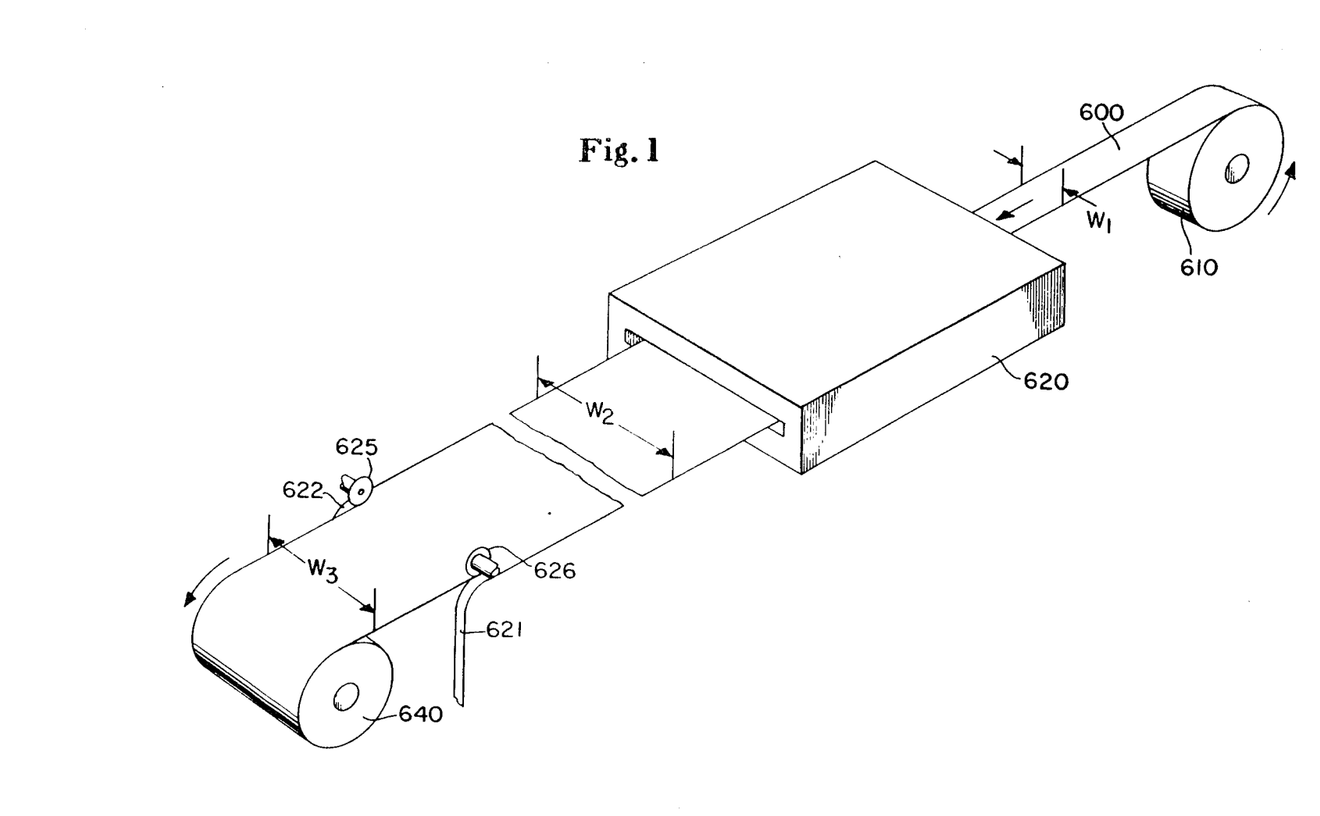
FIG. 1 is a simplified schematic view of a preferred method for forming a continuous roll of heat unstable elastomeric material which will shrink in a direction substantially parallel to the width of the roll upon the application of heat.

A typical tentering operation is schematically illustrated in FIG. 1. A web 600 of suitable heat stable elastomeric material is fed from a roll 610 into a heated tentering apparatus 620. The temperature of the tentering apparatus is below the crystalline melting temperature of the material. For materials such as the blend of ethylene propylene rubber and vinyl acetate mentioned earlier herein, the tentering apparatus is preferably maintained at a temperature of approximately 65° C. After softening, the web 600 is stretched from an initial width $W_1$, to approximately four times its initial width, as measured in a direction perpendicular to its direction of travel, i.e., as measured in the cross-machine direction. The stretched film is then allowed to cool to ambient temperature either with or without restraint. When cooled, the polymers are predominantly uniaxially cross-machine direction oriented and the film essentially retains its new dimension until such time as it is again subjected to an elevated temperature. The film is thus in a heat unstable state. (It should be noted that the material may still be elastic, even in its heat unstable state.) Because the outermost edges 621, 622 of the web 600 are clampled during the lateral stretching operation, they do not become stretched. Accordingly, the outermost edges 621, 622 of the heat unstable web 600 are preferably trimmed from the web by means of knives 625, 626 upon discharge form the tentering apparatus 620. This reduces the heat unstable web from a width $W_2$ to a final width $W_3$ prior to winding onto a roll 640. As will be pointed out hereinafter, the final width $W_3$ of the roll of heat unstable elastomeric material preferably corresponds to the overall length of the discrete elastically contractible segments cut from the web. It is of course recognized that a web of significantly greater width than that needed for a single elastomeric element could be prepared and thereafter slit into multiple rolls of the desired width.

Figure 2:
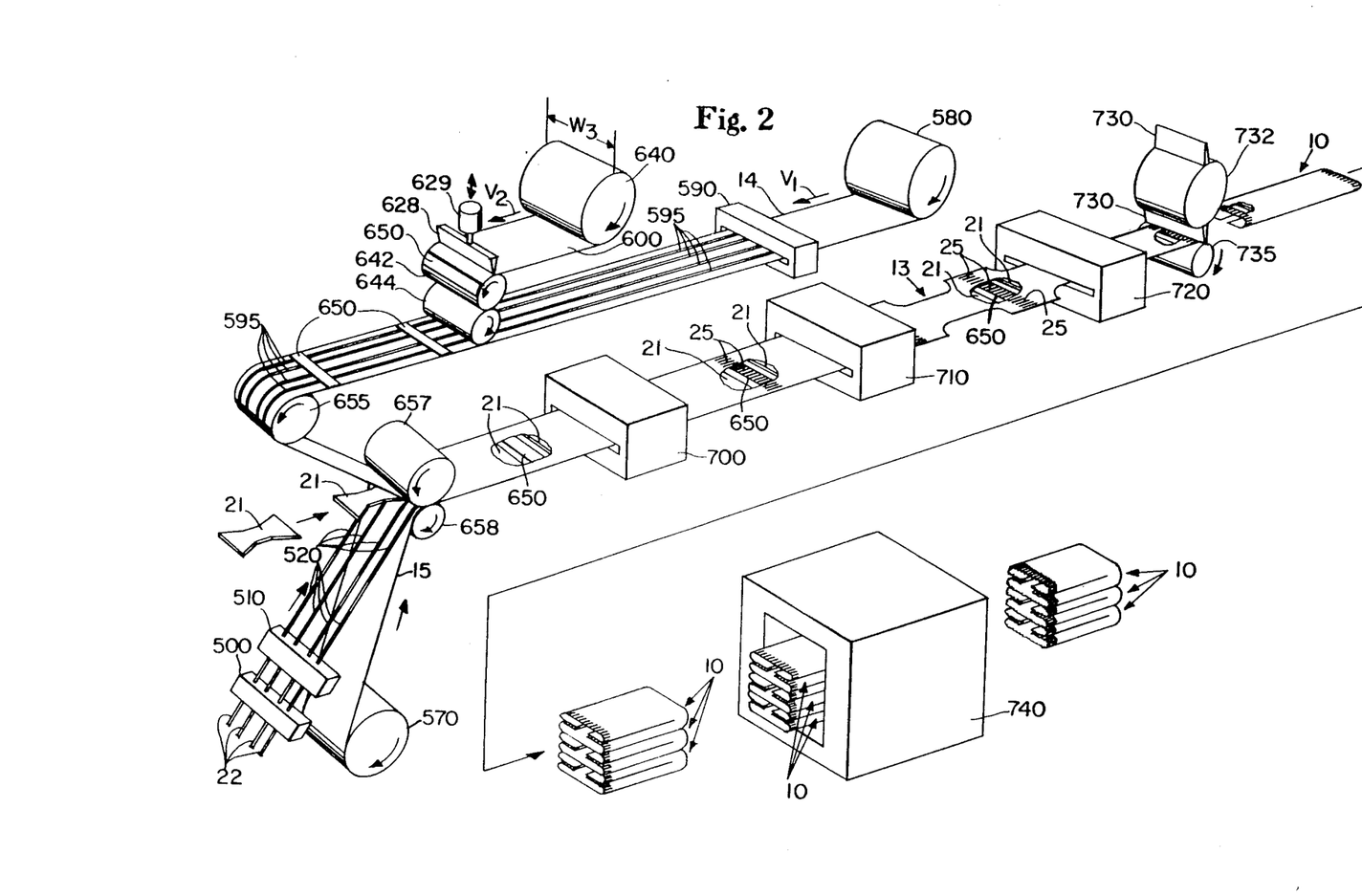
FIG. 2 is a simplified schematic view of a preferred method for attaching discrete elastically contractible segments cut from a heat unstable roll of elastomeric material, such as that shown in FIG. 1, to a continuously moving web used to form a multiplicity of interconnected elasticized articles which will shirr in a direction substantially perpendicular to the direction of web travel when the articles are cut from the web and subjected to heat in a substantially untensioned state.

FIG. 2 schematically discloses a particularly preferred method of practicing the present invention to produce a disposable diaper having both elasticized leg cuffs and elasticized waistbands. The legband attachment method is generally in accordance with the teachings of the aforementioned U.S. Pat. No. 4,081,301 issued to Buell on Mar. 28, 1978 and incorporated herein by reference, while the waistband attachment method is generally in accordance with the teachings of the aforementioned commonly assigned, copending patent application of L. Richard Chapman and Wayne I. Fanta entitled CONTINUOUS METHOD FOR ELASTICIZING DISCRETE ARTICLES CUT FROM A MOVING WEB IN A DIRECTION PERPENDICULAR TO WEB TRAVEL, Ser. No. 476,733, filed Mar. 18, 1983. In particular, a web of plastic backsheet material 14 is fed from a supply roll 580 at velocity $V_1$ to a glue applicator, shown schematically as 590, where a multiplicity of adhesive stripes 595 are applied to the uppermost surface of the web. A roll 640 of heat unstable elastomeric material 600 prepared generally in accordance with FIG. 1 and having an overall width $W_3$ is fed at a second velocity $V_2$ which is less than the velocity $V_1$ of backsheet web 14. Vacuum roll 642 and transfer roll 644 operate at peripheral velocities corresponding to the velocity $V_1$ of backsheet web 14. Accordingly, there is slippage between those portions of heat unstable elastomeric web 600 in contact with the periphery of vacuum roll 642 and vacuum roll 642.

In the illustrated embodiment, cutting knife 628 operated by cylinder 629 is timed to cut dimensionally heat unstable elastomeric segments 650 from the moving web 600. As can be seen from FIG. 2, the elastomeric segments 650 are spaced from one another by the faster moving suction roll 642 and transfer roll 644. The discrete segments 650 are held in contact along the periphery of suction roll 642 by means of vacuum applied to the interior surface of the roll and are transferred to transfer roll 644 by means of a positive pressure air blast at the point of tangency between the rolls. The transferred segment 650 is secured about the periphery of transfer roll 644 by means of vacuum until it approaches the point of tangency with moving backsheet web 14.

At the point of tangency, a positive pressure air blast is used to transfer the heat unstable elastomeric segments 650 across the small gap between the transfer roll 644 and the moving backsheet web 14. The beads of adhesive 595 utilized to assemble the various components of the diaper serve to hold the elastomeric segments 650 such that their overall length is oriented substantially perpendicular to the direction of web travel until such time as the segments are bonded at spaced locations along their length to the topsheet 15 and backsheet 14 by means of bonding apparatus 700. Bonding apparatus 700 preferably employs ultrasonic bonding procedures to provide regions of securement 25 between the segments 650 at spaced locations along their length and the topsheet 15 and backsheet 14.

For given diameters of suction roll 642 and transfer roll 644, the width of segments 650, as measured in a direction parallel to their direction of travel, and their spacing along the length of backsheet web 14 is controlled by adjusting the velocity $V_2$ of heat unstable elastomeric web 600 in relation to the velocity $V_1$ of backsheet web 14. In a typical embodiment, the speed $V_2$ of elastomeric web 600 is approximately ⅛ the speed $V_1$ of backsheet web 14.

As can be seen in FIG. 2, a web of topsheet material 15 is fed from a supply roll 570 between a pair of combining rolls 657 and 658 along with the backsheet web 14 having spaced elastomeric segments 650 attached thereto. Shaped abosrbent pad elements 21 are fed between combining rolls 657 and 658 in timed relation to the spaced elastomeric segments 650. The four elastic bands 22 utilized to provide elasticized leg cuffs are fed through suitable tensioning means 500, as generally disclosed in the aforementioned U.S. Pat. No. 4,081,301 to Buell, and adhesive 520 is applied to the stretched bands in spaced relation to the absorbent pads 21 and elastomeric segments 650 by means of glue applicator 510. Upon passage between combining rolls 657 and 658, a laminate diaper web is formed.

As can be seen from the partially broken away web segment following combining rolls 657 and 658, each heat unstable elastomeric segment 650 is positioned intermediate adjacent absorbent pad elements 21. The laminate web is thereafter passed through a suitable securement apparatus 700, which preferably comprises ultrasonic bonding means, wherein the heat unstable elastomeric segments 650 are bonded to the backsheet 14 and topsheet 15 of the diaper web to form regions of securement 25. This is best illustrated in the partially broken out segment of the web located downstream of securement apparatus 700.

The topsheet 15, backsheet 14, and each elastomeric segment 650 are affixed together by transverse regions of securement while the waist elastomeric elements are in their heat unstable state and all three elements are essentially fully, but not elastically, extended. The system is later heated (as with heated air) and the waist elastomeric element is allowed to return to its heat stable and elastic state.

Figure 3:
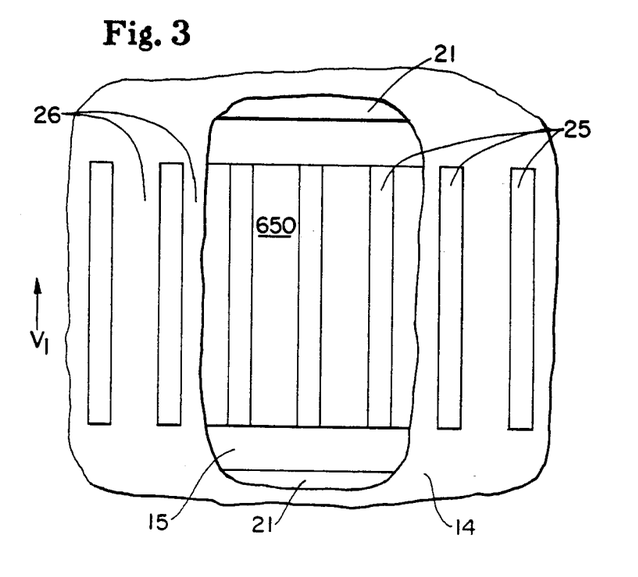
FIG. 3 is an enlarged, simplified schematic representation of the waistband area of the disposable diaper web of FIG. 2, said diaper web having its elastomeric waistband material shown in a heat unstable state after securement of the topsheet, the elastically contractible segment and the backsheet to one another.

Transverse regions of waistband securement of the type schematically illustrated in the web of FIG. 2 are shown in greatly enlarged form in FIG. 3. In this view, the elastomeric material is in its heat unstable and substantially untensioned state.

Transverse regions of securement 25 extend essentially across the whole width of each elastomeric segment 650, as measured in a direction parallel to web travel. The term "transverse" as used in this context refers to an orientation generally parallel to the direction of web travel generally illustrated in both FIGS. 1 and 2.

It should be noted that the transverse regions of securement 25 are preferably spaced and positioned so that they do not interfere with the elastic bands 22 when the bands are in a continuous, stretched condition, as generally illustrated in FIG. 2. This permits the unsecured portions of the stretched bands 22, i.e., those portions generally coinciding with the diaper waistband, to retract upon severance of the diapers from the web without causing shirring.

The term "essentially across" is used in this context to indicate that transverse regions of securement 25 need not extend absolutely across the entire width of the diaper waist, as measured perpendicular to the direction of web travel. It is, however, preferable that they extend sufficiently far across the width thereof to provide the channels discussed hereinafter.

In FIG. 3, transverse regions of securement 25 are shown as essentially regularly spaced unitary zones of sealing attaching each elastomeric segment 650 to topsheet 15 and backsheet 14. The precise means for providing the zones of sealing can be readily selected by those skilled in the art. Examples include ashesive attachment, solvent sealing and the like. Preferably, ultrasonic welding is used.

As illustrated in FIG. 3, the points of attachment of both topsheet 15 and backsheet 14 to the waist elastomeric element are in register (i.e. are coextensive). This is a preferred orientation, but the points of attachment of topsheet 15 to the waist elastomeric element can be offset from the adjacent points of attachment of backsheet 14 to the waist elastomeric element. In such a situation there will be offset transverse regions of securement on either side of the waist elastomeric element.

Transverse regions of securement 25 are preferably from about 0.15 to about 1.0 cm wide, as measured a direction perpendicular to web travel. They preferably extend across the width of the elastomeric segment, as measured in a direction parallel to web travel. They are also preferably regularly spaced, as measured perpendicular to web travel, but they can be nonuniformly spaced. They are most preferably from about 0.3 to about 1.5 cm apart as measured from center to center.

Following securement of the elastomeric segments 650 to the backsheet 14 and topsheet 15, the diaper web is thereafter passed into a side notching apparatus 710 wherein side notches are cut from the assembled web adjacent the narrow portion of each absorbent pad elements 21 to provide a crotch portion 13 in each of the interconnected disposable diapers. Securement tapes (not shown) are thereafter preferably applied to opposite edges of the rear waistband of each diaper by means well known in the art (and therefore not shown). In the illustrated embodiment, the web is thereafter preferably passed to a "c"-folding apparatus 720 wherein its cross-section is made to approximate that generally shown in FIG. 4 by folding diaper portions 763 and 764 into overlapping relation with diaper portion 765.

The "c"-folded web is thereafter preferably cut into discrete diapers 10 by one of the radially extending blades 730 mounted at the periphery of rotating cylinder 732. Blades 730 operate against a hard surfaced anvil roll 735 having a peripheral velocity $V_1$, equal to that of the moving web to effect severance of discrete diapers from the web. The cutting operation is timed in relation to movement of the web such that each elastomeric segment 650 is cut essentially in half. One half of the severed, heat unstable, elastomeric segment 650 forms the rear waistband of a first diaper while the other half of the heat unstable elastomeric segments forms the front waistband of the adjacent diaper.

The discrete diapers 10 are thereafter preferably folded about their midpoints, as shown in FIG. 2, stacked upon one another for cartoning and thereafter passed into a heating tunnel 740 in a substantially untensioned state. The heat applied in the tunnel is intended to elevate the temperature of the dimensionally heat unstable elastomeric segments contained in the diapers. The temperature is preferably elevated to a point below the crystalline melting temperature of the elastomeric segments to cause the segments to shrink in a direction perpendicular to the direction of web travel and return to a dimensionally heat stable and elastic condition. When carried out in accordance with the present invention, this produces a shirred or gathered waistband in the resultant diaper.

However, with a diaper severing operation of the type generally illustrated in FIG. 2, it has been observed that plastic flow of certain of the polymeric materials comprising the diaper, including the elastically contractible segment 650, results. The resultant plastic flow causes fusing of the elements comprising the article at each of the severed edges thus formed. This effect is most pronounced in situations where the web is folded into a c-fold, an e-fold or other multi-layer cross-section prior to severance, since more layers of material are fused to one another. This is illustrated in greatly enlarged form in FIG. 5, wherein the radially extending blade 730 employs a conventional prior art style linear cutting edge 737 aligned perpendicular to the direction of web travel. The resultant severed edge 760 of the diaper 10 is stiffened not only by fusing of the backsheet 14, the elastomeric segment 650 and the topsheet 15 to one another, but also by fusing of the overlapping portions 763 and 764 of the diaper to the unfolded portion 765 of the diaper.

It has further been observed that the amount of fusing and hence the stiffness of the severed edged 760 can increase with increased web speeds, and hence increased cutting speeds, to such a degree that the application of an external stimulus, such as heat, to impart shrinkage of the heat unstable, elastically contractible segment may be rendered to a large extent ineffective. This is believed due to the fact that the added resistance imparted by the fused and stiffened edges of the article is sufficient to negate or at least substantially reduce the relatively small shrinkage forces created in the heat unstable elastomeric segment when the segment is subjected to heating. The stiffening imposed by the severed edge 760 appears to be aided by the stiffness imparted by the absorbent core segment 21 located at the opposite edge of each of the transverse regions of securement 25 in resisting the aforementioned shrinkage forces.

While not wishing to be bound, it is believed that the fused edges of the article behave much like a rigid column to negate or at least substantially resist the relatively low shrinkage forces imposed by the elastically contractible segment when it is subjected to heating. Thus the tendency of the heat unstable elastomeric element to shrink substantially in a direction generally parallel to the desired direction of article shirring is, at least to a degree, overcome. To a large extent, the elastically contractible segment remains in a heat unstable condition upon cooling and exhibits a relatively low degree of elasticity. As a result, the article exhibits a very low degree of shirring and elasticity.

Figure 5:
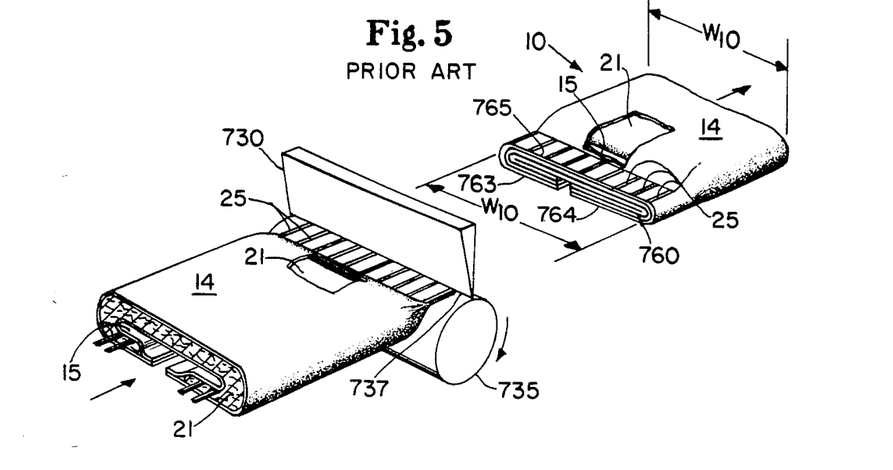
FIG. 5 is a greatly enlarged simplified schematic representation of the article cutting operation generally disclosed in FIG. 2, said operation employing a cutting blade having a conventional prior art linear cutting edge aligned substantially perpendicular to the direction of web travel.
Figure 6:
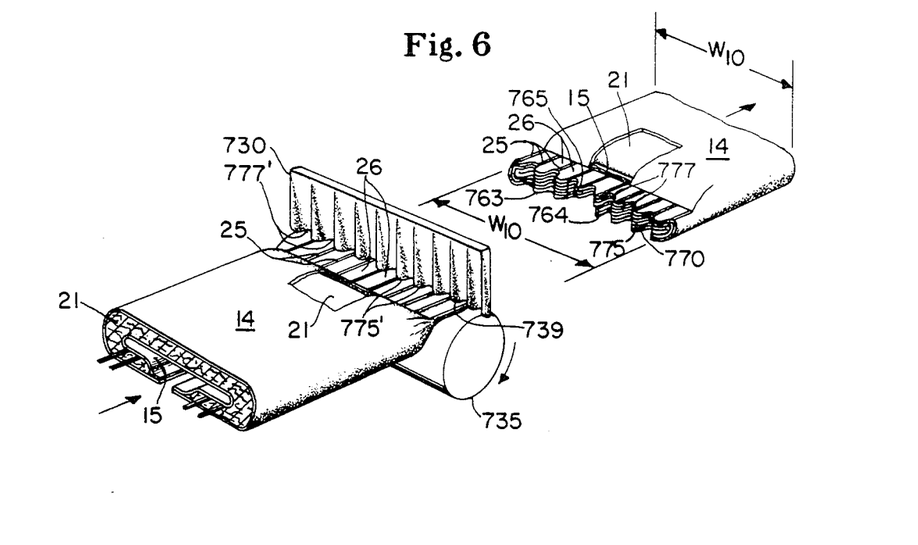
FIG. 6 is an enlarged, simplified schematic illustration generally similar to that of FIG. 5, but showing a preferred embodiment of the present invention wherein the cutting blade used to separate discrete articles from the continuous web employs a cutting edge of generally sinusoidal shape.

A preferred embodiment of the present invention which may be employed to overcome this unexpected resistance to shrinkage problem is generally illustrated in greatly enlarged form in FIG. 6. In the embodiment illustrated in FIG. 6, the radially extending blade 730 employs a sinusoidally shaped cutting edge 739 aligned perpendicular to the direction of web travel. The resultant severed edge 770 of diaper 10 exhibits a generally sinusoidal shape having peaks 775 corresponding to valleys 775' on cutting edge 739 of blade 730 and valleys 777 corresponding to peaks 777' on cutting edge 739 of blade 730. Although it is believed that the degree of fusing of backsheet 14, elastomeric segment 650 and the topsheet 15 to one another and the degree of fusing of the overlapping portions 763 and 764 of the diaper to the unfolded portion 765 thereof are generally comparable to that which is present in the linear severed edge 760 shown in FIG. 5, it has been observed that diapers employing a nonlinear severed edge 770 will undergo a much higher degree of shrinkage, as measured in a direction generally parallel to the overall orientation of the line of severance, than diapers with a linear severed edge 760 of the type generally shown in FIG. 5. As a result, the degree of waistband shirring, and hence the elasticity, in finished diapers cut from the web along a nonlinear line of severance is much greater than for comparably processed diapers cut from the web along a linear line of severance.

Thus, in accordance with the embodiment of the present invention herein illustrated, the diapers to be elasticized are cut from the web along a line of severance which is nonlinear. They are thereafter subjected to an external stimulus, such as heat, while in a substantially untensioned state to cause the elastomeric segments to shrink in a direction substantially parallel to the overall orientation of their nonlinear severed edges and assume a heat stable and elastic state. The resulting elastically contractible waistband assumes an essentially permanent set related to the folded configuration, such that even when the fused overlapping edges of the structure are separated, the essentially permanent set tends to cause the disposable diaper 10 to be shaped and to fit more closely about the trunk of the wearer.

Figures 7, 8:
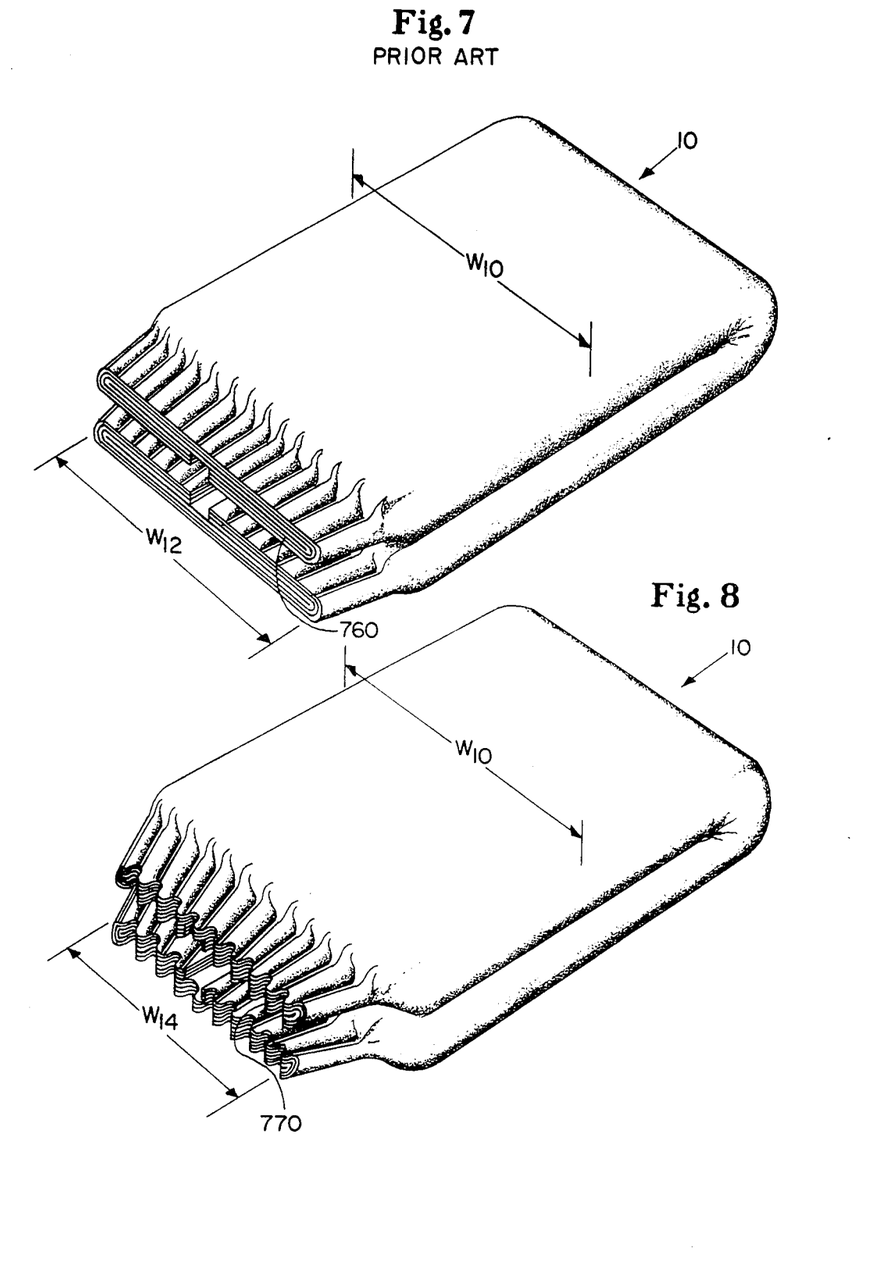
FIG. 7 is a simplified schematic illustration of a disposable diaper of the type generally shown in FIG. 5 after the diaper has been subjected to a heating operation to return the heat unstable elastically contractible segment to a heat stable condition.
FIG. 8 is a view generally similar to that of FIG. 7, but showing a diaper employing a nonlinear edge of the type generally illustrated in FIG. 6.

FIG. 7 is a perspective illustration of a disposable diaper 10 which is severed from the continuous web in the manner generally illustrated in FIG. 5 using a cutting blade 730 having a linear cutting edge 737. The condition of the diaper 10 shown in FIG. 7 is that which exists upon exit from the heating apparatus 740 illustrated in FIG. 2. As will be apparent from a comparison of FIGS. 5 and 7, the initial width $W_{10}$ of severed edge 760 has undergone a degree of reduction to a reduced width $W_{12}$ upon the application of heat to the elastically contractible segment 650 in the waistband of the diaper.

FIG. 8, on the other hand, illustrates an identically processed diaper which has been severed from the web utilizing a cutting blade 730 having a generally sinusoidally shaped cutting edge 739 to produce a generally sinusoidally shaped line of severance 770 at each waistband portion of the diaper. As will be noted from a comparison of FIG. 8 and FIG. 6, the initial width $W_{10}$ of the diaper waistband has undergone a considerably greater degree of shrinkage to a resultant width $W_{14}$ which, when all other conditions are maintained identical, will be substantially less than the resultant width $W_{12}$ of the diaper waistband shown in FIG. 7.

As will be appreciated by those skilled in the art, the greater the degree of shrinkage imparted to elastically contractible segment 650, the closer will be the areas of securement 25 which bond the topsheet, the elastically contractible segment and the backsheet to one another in the resultant elasticized diaper. Furthermore, the greater the degree of shrinkage in elastically contractible segment 650, the less will be the area of contact between the unsecured portions of the topsheet, the unsecured portions of the backsheet and the elastically contractible segment in the areas 26 generally shown in FIG. 3.

Because diapers of the present invention utilizing a nonlinear severed edge of the type generally shown in FIG. 6 undergo a greater degree of shrinkage than diapers employing a substantially linear edge 760 of the type generally shown in FIG. 5, the degree of elasticity exhibited in the finished diaper is, for identical processing conditions, substantially greater. Furthermore, it has been observed that consumers typically perceive the nonlinear severed edge 770 as being more aesthetically pleasing as well as softer when placed in contact with the wearer's skin in a tensioned condition.

EXAMPLES

Exemplary diapers produced according to the method of the present invention are constructed following the basic teachings of U.S. Pat. No. 3,860,003 issued to Buell on Jan. 14, 1975, as modified by the addition of an elasticized waistband generally in accordance with the teachings of the copending, commonly assigned patent application of L. Richard Chapman and Wayne I. Fanta, Ser. No. 476,733, filed Mar. 18, 1983 and entitled "CONTINUOUS METHOD FOR ELASTICIZING DISCRETE ARTICLES CUT FROM A MOVING WEB IN A DIRECTION PERPENDICULAR TO WEB TRAVEL". Thus, the diaper design hereinafter described provides for both front and rear elasticized waistbands.

The absorbent element comprises absorbent fluff having a density of about 0.09 g per $cm^3$ and a basis weight of about 1100 g per $M^2$ in the crotch portion and about 350 g per $M^2$ near the waist portions. It is generally hourglass-shaped and is about 38.7 cm long, about 25.4 cm wide at each of its laterally extending margins, and about 9.6 cm wide in the crotch portion. It is symmetrical about its longitudinal centerline, but asymmetrical about its lateral centerline in that the crotch portion is centered about 21.6 cm from the rear lateral margin.

The topsheet comprises a thermally bonded polypropylene material and the backsheet 0.04 mm thick polyethylene film. Both also are hourglass-shaped and are about 43.8 cm long and about 30.5 cm wide at their laterally extending margins.

During construction, the absorbent element is interposed between the topsheet and the backsheet which are essentially coextensive and coterminous. Hot-melt adhesive glue beads running parallel to the longitudinal centerline secure the backsheet to the absorbent element. They also secure the backsheet to the topsheet in the cuff regions.

The cuff portions of the diapers are elasticized by incorporating therein two elastic members in each longitudinally extending margin of the diaper at the crotch portion. Each is made of Fulflex 9211 and is 2.4 mm wide and 0.18 mm thick; their relaxed length is about 19.6 cm. They are extended to about 220% of their original lengths at the time of attachment generally in accordance with the teachings of the aforementioned U.S. Pat. No. 4,081,301 to Buell which is incorporated herein by reference. These elastic members are centered about the crotch portion. The pattern defined by the pair of members is centered about 9.4 cm from the longitudinal centerline of the diaper and parallel thereto. The two elastic members in each diaper margin are centered on parallel lines about 1.6 cm apart.

Each diaper waistband extends the lateral width of the diaper and is about 30.5 centimeters long; after cutting from the continuous web, each waistband is about 2.5 centimeters wide in the transverse direction, i.e., as measured in a direction parallel to the direction of web travel. The waist elastomeric element used in each waistband is the hereinbefore described ethylene propylene rubber blended with ethylene vinyl acetate. Each of the elastomeric elements comprises a discrete segment of material cut from a moving web of heat unstable material which has been tentered in a direction substantially perpendicular to the direction of web travel in the manner generally shown in FIGS. 1 and 2. The elements are applied to the moving web of interconnected diapers while in an untensioned condition in the manner generally disclosed in FIG. 2 so that the dimension corresponding to the final width $W_3$ of the web of elastomeric material 600 is aligned substantially perpendicular to the direction of web travel.

Prior to tentering in accordance with the process generally disclosed in FIG. 1, the elastomeric web 600 has an initial width $W_1$ of approximately 8 inches, i.e., approximately 20.3 centimeters, and an initial thickness of approximately 6 mils, i.e., 0.15 millimeters. Lateral stretching of the web was performed using a tentering apparatus 620 of the type available from Marshall & Williams Company of Providence, R.I. The tentering apparatus in question had three temperature zones, each being approximately 10 ft. in overall length. The web 600 was fed in a heat stable condition from a roll 610 into the first 10 ft. long zone at ambient temperature and without any lateral stretching. Approximately 1 inch, i.e., 2.54 centimeters, of outermost edges 621,622 of the web was gripped by the tentering apparatus. The central portion of the web 600 measuring approximately 6 inches, i.e., approximately 15 centimeters, in width, was subjected to lateral stretching over the last two 10 ft. long sections of the apparatus 620. The last two 10 ft. long sections were maintained at a temperature between about 140° and about 155° F., i.e., between about 60° C. and about 68° C., and the central portion of the web was stretched from an initial width of about 6 inches, i.e., about 15 centimeters, to a width of approximately 24 inches, i.e, approximately 60 centimeters, as it passed through the last two 10 ft. long zones of the apparatus. After discharge from the third 10 ft. long zone of the tentering apparatus, the web was allowed to cool without restraint, resulting in a degree of contraction to a final width $W_2$ of approximately 19 inches, including the 1 inch gripping portions of outermost edges 621,622. After cooling, the elastomeric web 600 is in a heat unstable condition. The overall thickness of the web 600 in the centrally located section averaged approximately 1.5 mils, i.e., 0.0038 millimeters. Prior to use in the process generally disclosed in FIG. 2, the outermost edges 621,622, including the portions gripped by the tentering apparatus, are preferably removed by slitting, e.g., as by knives 625,626 to produce a final width $W_3$ which corresponds to the overall length of the waistband segments to be affixed to the diapers. In the exemplary embodiment herein described, the resultant width $W_3$ of the elastomeric heat unstable web 600 is approximately 30.5 centimeters.

In the foregoing example, the speed of web travel through the tentering apparatus 620 is between about 20 and about 26 feet per minute.

When attached in the manner generally shown in FIG. 2, each discrete segment of heat unstable elastomeric material cut from roll 640 is about 30.5 centimeters long (as measured perpendicular to the direction of web travel) and about 5.0 centimeters wide (as measured parallel to the direction of web travel). Each discrete segment of heat unstable elastomeric material is secured to both the topsheet and the backsheet at spaced locations along its length (as measured perpendicular to the direction of web travel) in the manner schematically shown in FIG. 2. At the time of securement, the topsheet and the backsheet are in fully extended configurations. No sealing of the heat unstable elastomeric waistband elements in the areas coinciding with the stretched elastic legbands is carried out to ensure that the legbands remain free to retract to their unstretched condition in their unadhered areas when the individual diapers are severed from the continuous web.

As will also be clear from an inspection of FIG. 2, each heat unstable elastomeric segment bridges the waistband portion of adjacent interconnected diapers in the moving web. Accordingly, when the diapers are severed from the web as generally shown in FIG. 2, the approximately 5 centimeter wide elastomeric segment is cut at approximately its midpoint. Half of the strip forms the rear waistband of one diaper while the other half of the strip forms the front waistband of the adjacent diaper.

In the exemplary diaper embodiment herein described, transverse regions of securement comprising discrete zones of ultrasonic welds are used to affix each waist elastomeric element to both the topsheet and to the backsheet. The transverse regions of securement each comprise ten discrete elliptical zones of ultrasonic welds each having a major axis of about 1.9 mm and a minor axis of about 1.0 mm; each individual ellipse is set with its major axis at an angle of about 45° to the transverse direction. The transverse regions of securement are generally regularly spaced along each waistband and their centers are about 6.4 mm apart.

Adhesive fastening tapes were adhesively affixed to the diaper.

Figure 4:
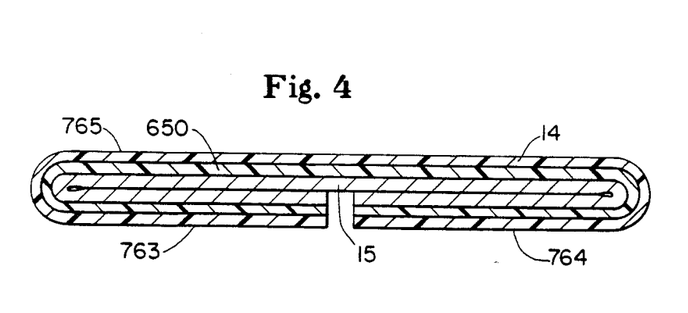
FIG. 4 is an enlarged, simplified schematic cross-section of the disposable diaper web shown in FIG. 2 after the web has been caused to assume a C-fold configuration, but prior to the cutting or heating operations shown in FIG. 2, said cross-section being taken at a point coinciding with the elastomeric segment used to form the elasticized waistband.

The assembled diaper web is folded into an overlapping e-fold configuration, i.e., a configuration generally similar to the c-fold embodiment shown in FIGS. 4, 5 and 6, except that the diaper portions 763 and 764 overlap one another at points coinciding with the waistband of the diaper. The width of the unfolded diaper portion 765 (i.e. the width corresponding to width $W_{10}$ in FIG. 5) measured approximately 12 centimeters. The diapers were cut from a web moving at a continuous velocity $V_1$ of approximately 750 feet per minute using a cutting blade 730 having a sinusoidally shaped cutting edge 739 exhibiting a regular peak-to-corresponding-peak frequency of approximately 6 mm. and a total peak-to-valley amplitude of approximately 2 mm. After cutting from the web, the discrete diaper embodiments were folded approximately about their midpoints, collected into multi-unit stacks for cartoning and heated with air at about 68° C. for a period of approximately three seconds.

Following the heating operation the exemplary diapers were allowed to cool to ambient temperature. The diapers exhibited a nonlinear severed edge having an unstretched width corresponding, to width $W_{14}$ in FIG. 8, as measured at severed edge 770, of approximately 10 centimeters. When unfolded, the diapers exhibited an acceptable degree of elasticity in their waistband portions.

As indicated hereinbefore, the diaper embodiments described in detail in conjunction with the present method invention are intended to be illustrative of articles to which the present invention has particular application. Other elasticized articles produced in continuous web form and embodying elastically contractible segments which tend to cause shirring in a direction substantially parallel to the overall orientation of the line of severance can be produced with equal facility by applying the teachings herein contained.

In the foregoing discussion, the elastomeric waistband material which was affixed to the diaper in a heat unstable state and was then treated to cause it to be transformed into a heat stable and elastic state has been discussed in terms of a "heat unstable" elastomer. More broadly, the elastomeric materials useful herein are those materials that have a dimensionally unstable state relative to some other dimensionally stable and elastic state and which can be caused to be transformed from the unstable to the stable state by the application of any form of energy or by any other convenient treatment. The most convenient and the most practical form of energy is heat, and the materials are described in such terms herein.

Still further, the present invention has been described in terms of an elastomeric material which is affixed to the diaper in its unstable state and is later transformed to its stable and elastic state. While, in general, the stable state is an absolute state, it is not necessary that it be. It is only required that the state following treatment be relatively more stable than the state preceding treatment and that the state following treatment be sufficiently stable for practical use. It is, of course, necessary that the material be elastic in its stable state.

Finally, it is recognized that the precise nature of the nonlinear line of severance will have an effect upon the amount of resistance imparted by the fused and severed edge of the article. In the practice of the present invention it has been observed that the resistance to compression or "beam strength" of the fused and severed edge is in general reduced by the inclusion of stress concentrating features in the severed edge. In a very simple embodiment, these stress concentrating features may comprise slits oriented generally perpendicular to the severed edge. In other embodiments, more complex patterns, such as sinusoidally shaped severedc edges may be employed. In general, the effectiveness of the stress concentrating feature in lowering a fused and severed edge's resistance to compression increases with the size of the stress concentrating feature and its frequency along the edge in question.

While particular embodiments of the present invention have been illustrated and described, it will be obvious to those skilled in the art that various changes and modifications can be made without departing from the spirit and scope of the invention. It is intended to cover in the appended claims all such modifications that are within the scope of this invention.

What is claimed is:

1. A disposable diaper having at least one waistband, said diaper comprising a topsheet, a backsheet, and an absorbent element interposed between said topsheet and said backsheet, said waistband having an elastic element interposed between said topsheet and said backsheet and being coextensive with the outer margin of said waistband, said outer margin of said waistband being nonlinear along its length, said diaper being formed by a method comprising the steps of:
   (a) subjecting a web of elastomeric material capable of exhibiting dimensionally heat stable and dimensionally heat unstable states to stretching while said web is at an elevated temperature which is less than its crystalline melting temperature;
   (b) allowing said elastomeric web to cool to ambient temperature while in a stretched condition to establish a heat unstable state in the material comprising said web;
   (c) feeding said web of elastomeric heat unstable material in a direction substantially parallel to a moving web of interconnected articles;
   (d) severing discrete segments of said elastomeric heat unstable material from said elastomeric web in a direction substantially perpendicular to the direction of web travel, whereby each of said discrete segments of elastomeric material has its length oriented parallel to the direction of said lateral stretching and its width oriented in a direction substantially parallel to the direction of web travel;
   (e) transferring said discrete, severed segments of elastomeric material in a substantially untensioned condition with their lengths oriented substantially perpendicular to the direction of web travel to said moving web of interconnected articles at isolated, predetermined locations along the length of said web;
   (f) securing said discrete segments of substantially untensioned, heat unstable elastomeric material to said web of interconnected articles at predetermined spaced locations along the length of said segments, as measured in a direction substantially perpendicular to the direction of web travel;
   (g) severing each of the interconnected articles from one another at predetermined points coinciding with said elastically contractible segments along a nonlinear line of severance oriented substantially perpendicular to the direction of web travel, thereby dividing each of said elastically contractible segments into at least two portions and forming a multiplicity of discrete articles each having at least one portion of said segment of substantially untensioned elastomeric material in a heat unstable condition fused to said article along at least a portion of said nonlinear severed edge; and
   (h) heating said discrete articles to an elevated temperature which is less than the crystalline melting temperature of said heat unstable segments of substantially untensioned elastomeric material, thereby causing said elastomeric material to contract along the fused portions of said nonlinear severed edge, to become heat stable and elastic, and to shirr said articles in a direction substantially parallel to the orientation of said nonlinear severed edge.

* * * * *

UNITED STATES PATENT AND TRADEMARK OFFICE
CERTIFICATE OF CORRECTION

PATENT NO. : 4,563,185
DATED : January 7, 1986
INVENTOR(S) : Godfrey Reiter

It is certified that error appears in the above-identified patent and that said Letters Patent is hereby corrected as shown below:

Column 1, line 26, "serverance" should read -- severance --.

Column 2, line 2, "descirbe" should read -- describe --.

Column 8, line 25, "clampled" should read -- clamped --.

Column 8, line 29, "form" should read -- from --.

Column 9, line 43, "abosrbent" should read -- absorbent --.

Column 11, line 57, "edged" should read -- edge --.

Column 17, line 2, "severedc" should read -- severed --.

Signed and Sealed this

Eighth Day of April 1986

[SEAL]

Attest:

DONALD J. QUIGG

Attesting Officer

Commissioner of Patents and Trademarks